(12) United States Patent
Alexander et al.

(10) Patent No.: US 7,680,316 B2
(45) Date of Patent: Mar. 16, 2010

(54) IMAGING DEVICE AND METHODS TO DERIVE AN IMAGE ON A SOLID PHASE

(75) Inventors: John Alexander, New South Wales (AU); Michael Bruce Chandler, New South Wales (AU)

(73) Assignee: Medsaic Pty Ltd., Eveleigh, New South Wales (AU)

( * ) Notice: Subject to any disclaimer, the term of this patent is extended or adjusted under 35 U.S.C. 154(b) by 1218 days.

(21) Appl. No.: 10/547,235

(22) PCT Filed: Mar. 1, 2004

(86) PCT No.: PCT/AU2004/000264

§ 371 (c)(1),
(2), (4) Date: Aug. 26, 2005

(87) PCT Pub. No.: WO2004/077031

PCT Pub. Date: Sep. 10, 2004

(65) Prior Publication Data

US 2006/0238846 A1    Oct. 26, 2006

(30) Foreign Application Priority Data

Feb. 28, 2003    (AU) .............................. 2003900924

(51) Int. Cl.
*G06K 9/00*    (2006.01)
(52) U.S. Cl. ..................................................... 382/133
(58) Field of Classification Search ......... 382/128–134; 356/7–11, 39–50; 250/200–230, 455–465
See application file for complete search history.

(56) References Cited

U.S. PATENT DOCUMENTS 5,377,003 A * 12/1994 Lewis et al. .................. 356/300

(Continued)

FOREIGN PATENT DOCUMENTS

WO    WO 00/79326 A1    12/2000

(Continued)

OTHER PUBLICATIONS

Goh, J. B., et al., *Analytical Biochemistry*, 313:262-266 (2003).

(Continued)

*Primary Examiner*—Samir A. Ahmed
*Assistant Examiner*—Atiba O Fitzpatrick
(74) *Attorney, Agent, or Firm*—Perkins Coie, LLP

(57) ABSTRACT

An imaging device (46) comprises a carrier stage (12a) for carrying a sample slide (14a) including a micro-array of cellular binding event samples, a linear light source (37a) for illuminating the sample slide (14a), and a motor drive (16a) for moving the carrier stage (12a) relative to the sample slide (14a) such that successive portions of the sample slide (14a) are illuminated by the light source (37a). A digital optical line scan camera system (44a) is disposed such that, in use, it captures substantially only the successive portions of light rays (40a) which emerge from the sample slide at an offset angle relative to light rays (42a) from light source transmitted through and emerging from the sample slide (14a) to generate a series of linear dark field images arranged to be reconstructed into a composite image of the sample slide or array of samples.

13 Claims, 12 Drawing Sheets

U.S. PATENT DOCUMENTS

| | | | |
|---|---|---|---|
| 5,386,112 A * | 1/1995 | Dixon | 250/234 |
| 5,898,503 A | 4/1999 | Keller et al. | |
| 5,912,456 A | 6/1999 | Melendez et al. | |
| 5,946,083 A | 8/1999 | Melendez et al. | |
| 6,111,248 A | 8/2000 | Melendez et al. | |
| 6,111,652 A | 8/2000 | Melendez et al. | |
| 6,160,618 A | 12/2000 | Garner | |
| 6,180,415 B1 * | 1/2001 | Schultz et al. | 436/518 |
| 6,326,612 B1 | 12/2001 | Elkind et al. | |
| 6,415,235 B1 * | 7/2002 | Bartholomew et al. | 702/28 |
| 6,436,348 B1 * | 8/2002 | Ljungmann et al. | 422/63 |
| 6,594,018 B1 | 7/2003 | Bartholomew et al. | |
| 6,687,419 B1 * | 2/2004 | Atkin | 382/284 |
| 2001/0043884 A1 * | 11/2001 | Essenfeld et al. | 422/99 |
| 2002/0025534 A1 * | 2/2002 | Goh et al. | 435/7.1 |
| 2003/0167130 A1 | 9/2003 | Soussaline et al. | |
| 2004/0017150 A1 | 1/2004 | Fricke et al. | |
| 2005/0254704 A1 * | 11/2005 | Komiya et al. | 382/162 |

FOREIGN PATENT DOCUMENTS

| | | |
|---|---|---|
| WO | WO 01/11340 A1 | 2/2001 |
| WO | WO 01/34846 A2 | 5/2001 |
| WO | WO 03/050538 A1 | 6/2003 |

OTHER PUBLICATIONS

Spreeta Technology Overview: [online] *Texas Instruments*, Oct. 30, 2003 [retrieved on Aug. 24, 2005]. Retrieved from the Internet: <URL: http://www.ti.com/sc/docs/products/msp/control/spreeta/what.htm>.

* cited by examiner

IMAGING DEVICE AND METHODS TO DERIVE AN IMAGE ON A SOLID PHASE

FIELD OF THE INVENTION

The present invention relates broadly to an imaging device and to a method of deriving an image of samples on a transparent solid phase such as a sample slide.

BACKGROUND OF THE INVENTION

The analysis of samples such as cells, for example those obtained from a patient, bound to an arrangement of binding partners, such as a protein micro-array on a glass slide has been proposed as a diagnostic tool.

Similarly, the analysis of the presence of fluorescent markets indicative of the presence of particular molecules such as proteins in a sample has been proposed as a diagnostic tool.

It is desirable to provide a device for capturing digitised patterns of such samples to facilitate the use and implementation of such a diagnostic tool. It is further desirable to provide a device which can be made readily available for widespread usage over a distributed network of pathology laboratories and research facilities.

In at least preferred embodiments, the present invention seeks to provide a compact imaging device and a method of deriving an image of samples on a sample slide suitable for implementation of such a diagnostic tool.

SUMMARY OF THE INVENTION

According to a first aspect of the invention there is provided an imaging device comprising:
a carrier stage for carrying a sample slide,
a light source for illuminating the sample slide, said sample slide including an array of samples,
drive means for moving the carrier stage relative to the sample slide such that successive portions of the sample slide are illuminated by the light source;
a digital optical camera system disposed such that in use, it captures substantially only said successive portions of light rays which emerge from the sample slide at an offset angle relative to light rays from light source transmitted through and emerging from the sample slide to generate a series of partial images arranged to be reconstructed into an image of the sample slide or array of samples.

Preferably, the light source is a linear light source arranged to emit a substantially narrow beam, whereby successive portions of the sample slide that are illuminated are band-like portions, and whereby the series of partial images are linear images.

Conveniently, the digital optical camera system is disposed such that, in use, it receives substantially only light rays which are diffracted or otherwise deflected at said array of samples on the sample slide.

Typically, the digital optical camera system includes discriminator means for preventing light rays which are not diffracted or otherwise deflected by the sample array from being captured by the camera system.

Advantageously, the discriminator means includes at least one reflector positioned to direct diffracted or otherwise deflected light rays emerging from the sample slide at the offset angle towards an imaging lens of the camera system.

The digital optical camera system typically includes a line scan capable camera capable of sensing a linear image.

The digital optical camera system may be disposed such that, in use, light rays emitted from fluorescent markers on the sample slide are captured.

Conveniently, the digital optical camera system is arranged to operate in at least two modes, namely a diffraction or deflection mode, in which light rays diffracted or otherwise deflected at the array of samples on the sample slide are captured by the camera, and a fluorescent mode, in which light rays emitted from fluorescent markers on the array of samples are captured.

The digital optical camera system may be arranged to operate in the deflection or diffraction mode when the drive means moves the carrier stage in a first direction and is arranged to operate in the fluorescent mode when the drive means is moves the carrier stage in a second direction.

The optical camera system may be arranged to detect light rays in both the visible and non-visible portions of the spectrum.

Typically the sample comprise an array of cells bound to binding partners on the sample slide.

In once form of the invention, the imaging device comprises a sampling compartment in which, in use, the carrier stage is located, and an electrical component compartment, wherein the electrical components compartment is fluid sealed from the sampling compartment, whereby, in use, fluid contamination of components inside the electrical components compartment from the sampling compartment is inhibited, the carrier stage including a tray element disposed, in use, underneath the sample slide for collecting fluid spilled from the sample slide.

The imaging device may include an interface unit for interfacing to devices of a group including at least one of an external reference database, an external storage database, an external PC, and an external printer.

Advantageously, the partial images and the reconstructed images are dark field images.

The invention extends to an imaging system including an imaging device of the type described above and processor means for processing the image of the sample slide or array of samples to provide image intensity values representative of the array of samples for comparative purposes.

The invention further extends to the processor means for processing the image of the sample slide or array of samples to provide image intensity values representative of the array of samples for comparative purposes.

Advantageously, the processor means is arranged to normalise the image by using known reference samples on the slide to locate each sample on the slide and to scale the intensity of each sample.

The processor means is preferably arranged to locate each sample by applying a reference matrix or grid on the basis of the known reference sample arranged to scale the intensity of the samples within each square in the grid using the reference samples to establish the range of the scale, and is further arranged to generate a normalised intensity values from the image.

The invention still further provides a method of deriving an image representative of samples on a sample slide, the method comprising
providing a sample slide including an array of samples
loading the sample slide onto a carrier stage
illuminating at least a portion of the sample slide,
moving the carrier stage relative to the sample slide such that successive portions of the sample slide are illuminated by the light source; and
capturing substantially only successive diffracted or otherwise deflected portions of light rays which emerge from the sample slide to generate a series of partial images arranged to be reconstructed into an image of the array of samples.

Preferably, successive portions of the sample slide that an illuminated are band-like portions illuminated by ultilising a linear light source, and whereby the series of partial images are captured as linear images.

The method advantageously comprises the step of capturing substantially only light rays diffracted or otherwise deflected by or at samples on the sample slide.

Preferably, the method further comprises utilising reference samples disposed in a manner such that light rays diffracted or otherwise deflected at the reference samples are captured during the deriving of the image, for indicating the biological condition of the sample and/or intensity scaling.

The method may include processing the reconstructed image to arrive at a molecular profile which is comparable with a library of molecular profile signatures.

The method may further include generating image intensity values for each sample, generating a contour map of image intensities identifying image objects within contour lines, and placing a virtual grid over said objects.

The method typically further includes deskewing the image, obtaining an enhanced grid, and calculating X-Y co-ordinates from the enhanced grid.

Preferably, the method includes calculating an averaged corrected intensity for each sample, whereby at least two sets of identical samples are provided on the slide, and normalising the intensity data associated with each sample on the basis of reference samples and duplicate samples.

The method further extends to an imaging processing method for processing an image of the type obtained from the device, as well as to a computer readable medium having stored thereon executable instructions for causing a computer to carry out the method,

BRIEF DESCRIPTION OF THE DRAWINGS

Preferred embodiments of the present invention will now be described, by way of example only, with reference to the accompanying drawings.

DETAILED DESCRIPTION OF THE EMBODIMENTS

In the preferred embodiments described, the present invention provides an imaging device and methods of taking a sequential series of dark field linear images to construct an offset planar image of a bound cellular array or a sample containing fluorescent markers, suitable for identifying a molecular profile thereby implementing a diagnostic tool which utilises analysis of samples on a sample slide or other transparent solid phase support media. The offset planar image is digitally re-assembled to provide a digital array which can be passed on to a pattern matching program or the like for molecular profile identification.

Figure 1:
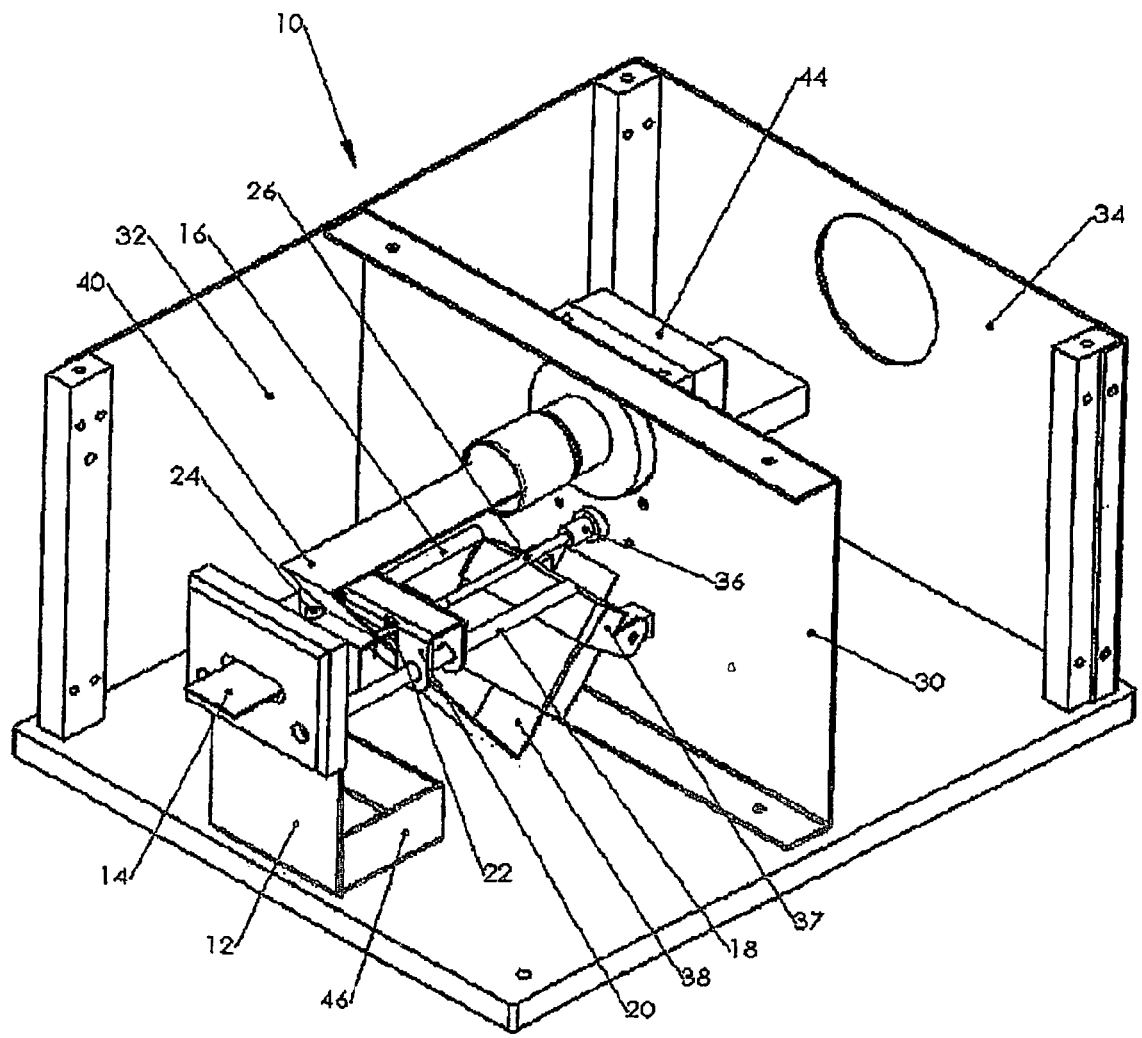
FIG. 1 is a schematic perspective drawing illustrating an imaging device of a first embodiment of the present invention, with parts of the housing removed and only selected components shown for clarity.

FIG. 1 shows a schematic diagram of an imaging device 10 embodying the present invention. The device 10 comprises a carriage 12 for mounting a slide 14 for analysis of a bound cellular array (102 in FIG. 3) bound on the slide 14. The carriage 12 comprises two guiding rods 16, 18 onto which a slide holder 20 is movably mounted. The holder 20 comprises two biasing elements in the form of spring members 22, 24 for releasably receiving the slide 14.

Figure 2:
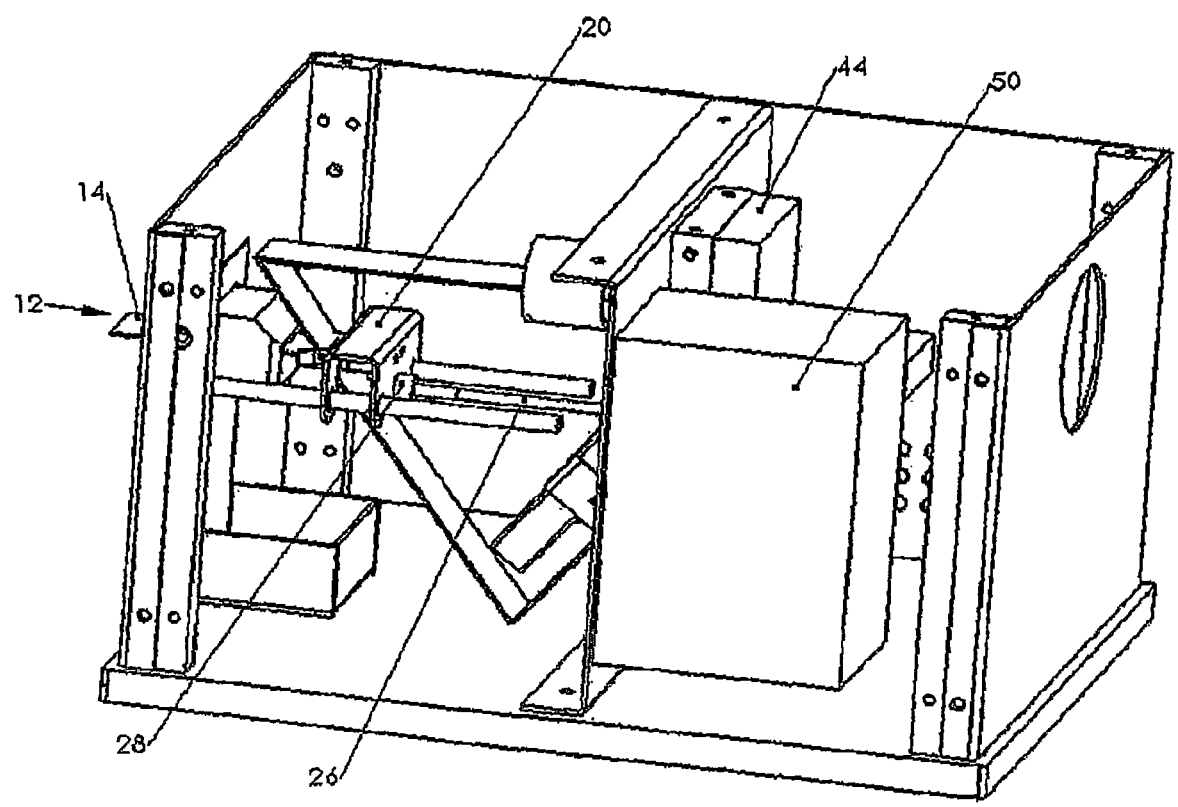
FIG. 2 is a schematic drawing illustrating a different view of the imaging device of FIG. 1, with some of the housing removed and only selected components shown for clarity.

The imaging device 10 further comprises a magnetic pull stepper drive mechanism of which a pull bar 26 is shown in FIG. 1. As can be more clearly seen in FIG. 2, the pull bar 26 comprises a magnetic end portion 28 for connecting to the holder 20, which is made of a suitable magnetic material. The use of a magnetic pull stepper drive mechanism in the example embodiment has the advantage of providing a readily releasable connection between the pull bar 26 and the holder 20, to facilitate removal of the carriage 12 for cleaning or other maintenance purposes of the carriage and/or the interior of the imaging device 10.

Figure 3:
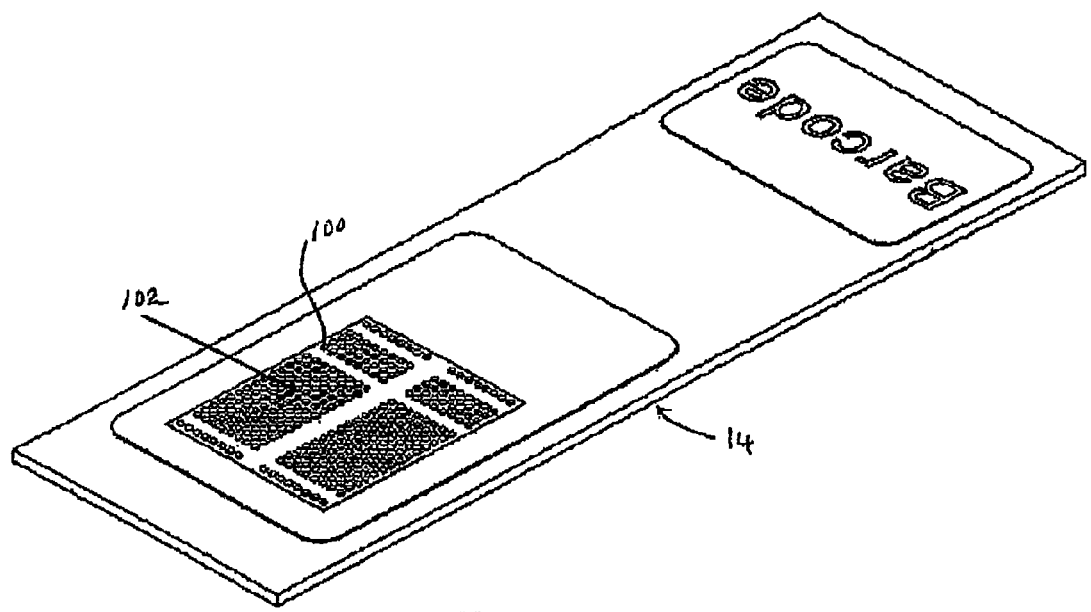
FIG. 3 is a schematic drawing illustrating a perspective view of an example sample slide for use in an imaging device embodying the present invention.

FIG. 3 shows an isometric drawing of an example of the sample slide 14. The slide 14 comprises a plurality of indents 100 containing localised binding events. In particular, each of which typically contains different binding ligands to provide a bound array of binding partners 102. The slide 14 is formed from a substantially optically transparent material, such as glass or suitable plastic material such as polystyrene or polycarbonate (Cyrolon TX-V), polyvinyl alcohol, nylon or composites thereof. Such supporting materials are either untreated or treated with absorbent or binding enhancing coatings to facilitate the binding of each binding partner. In the embodiment, FAST from Schleicher and Schuell Bio-Science, Inc, of 10 Optical Avenue, Keene N.H. 03431 USA slides were used. These slides are manufactured from high quality glass with a nitro-cellulose coating. It will be appreciated by a person skilled in the art that there are several chemical and physical approaches to secure protein based material on said solid phase materials. Each slide may contain up to 1,000 or more binding events.

Figure 3A:
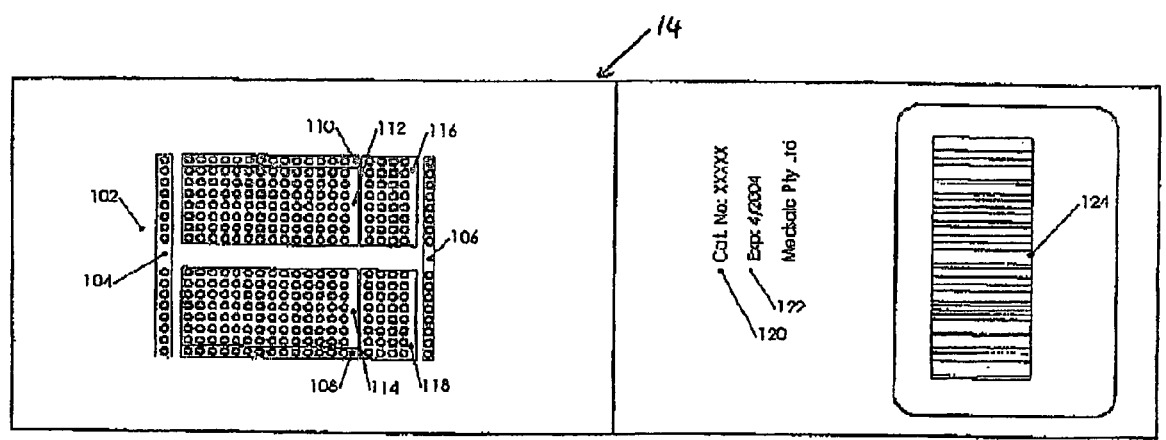
FIG. 3A is a top plan view of the sample slide of FIG. 3.

FIG. 3A shows a top plan view of the sample slide 14 for use as a diagnostic tool in diagnosing leukaemia. The array of binding partners 102 includes rows of serial calibration dots 104 and 106 for alignment and intensity correction purposes, and typically covering the full expected optical range, from lightest to darkest. Outer peripheral rows of calibration dots 108 and 110 formed from reference binding partners such as monoclonal antibodies representative of the binding partners expected to yield the darkest image. In conjunction, the outer peripheral calibration dots define the spatial boundary of said binding events for facilitating image construction. The serial calibration dots 104 and 106 may be formed from monoclonal antibodies varying from predetermined high to low concentrations by progressive dilution. Arrays of a diagnostic markers 112 and 114 are located centrally on the slide, which further includes a sub-array of therapeutic markers 116 and a sub-array of diagnostic and QC markers 118. The arrays 112 and 114 are substantially identical so they can be used for cross-checking purposes, and the results averaged for a more reliable outcome. Further information on the slide includes a catalogue number 120, an expiry date 122 and a bar code 124 encoding this and other information on the slide.

Returning now to FIG. 1, the pull bar 26 extends through a dividing wall 30 within the imaging device 10, which divides the interior of the optical device 10 into a sampling area 32, and an electrical components area 34. In the example embodiment, the dividing wall 30 is adapted such that a fluid seal is created between the sampling area and the electrical components area, whereby contamination of electrical components inside the electrical components area 34 from the sampling area 32 is inhibited.

The pull bar 26 extends through the dividing wall 30 via a sealing member 36, which is adapted to allow movement of the pull bar 26, while maintaining a fluid seal between the sampling area 32, and the electrical components area 34. A drip tray 46 may be provided with the carriage 12 for collecting fluid that may drip from the slide 14 during the analysis.

The imaging device 10 further comprises an LED bracket 37 for emitting a substantially planar beam of light 38 for taking an image of the bound cellular or protein array 102 (FIGS. 3 and 3A) mounted on the slide 14. The beam 38 is initially reflected by a first mirror (not shown) such that it is directed towards the slide from the bottom thereof. Above the slide, a second mirror (not shown) is utilised to direct a portion 40 of the initial light beam containing rays which have been diffracted or otherwise deflected at bound binding partners (not shown) towards the digital camera device. The camera takes successive linear images of the offset planar light diffracted or otherwise deflected at the slide or solid phase equivalent, as it moves through the band of light emitted from the light source at a speed consistent with image capture capability of said camera. It will be appreciated by a person skilled in the art, that through suitable adjustment of the mirror element (not shown) for directing the deflected beam portion the imaging device 10 can be adapted in a manner such that substantially only a diffracted or otherwise deflected beam portion 40 is captured in the line scan camera 44 for deriving an image of the bound array.

Figure 4:
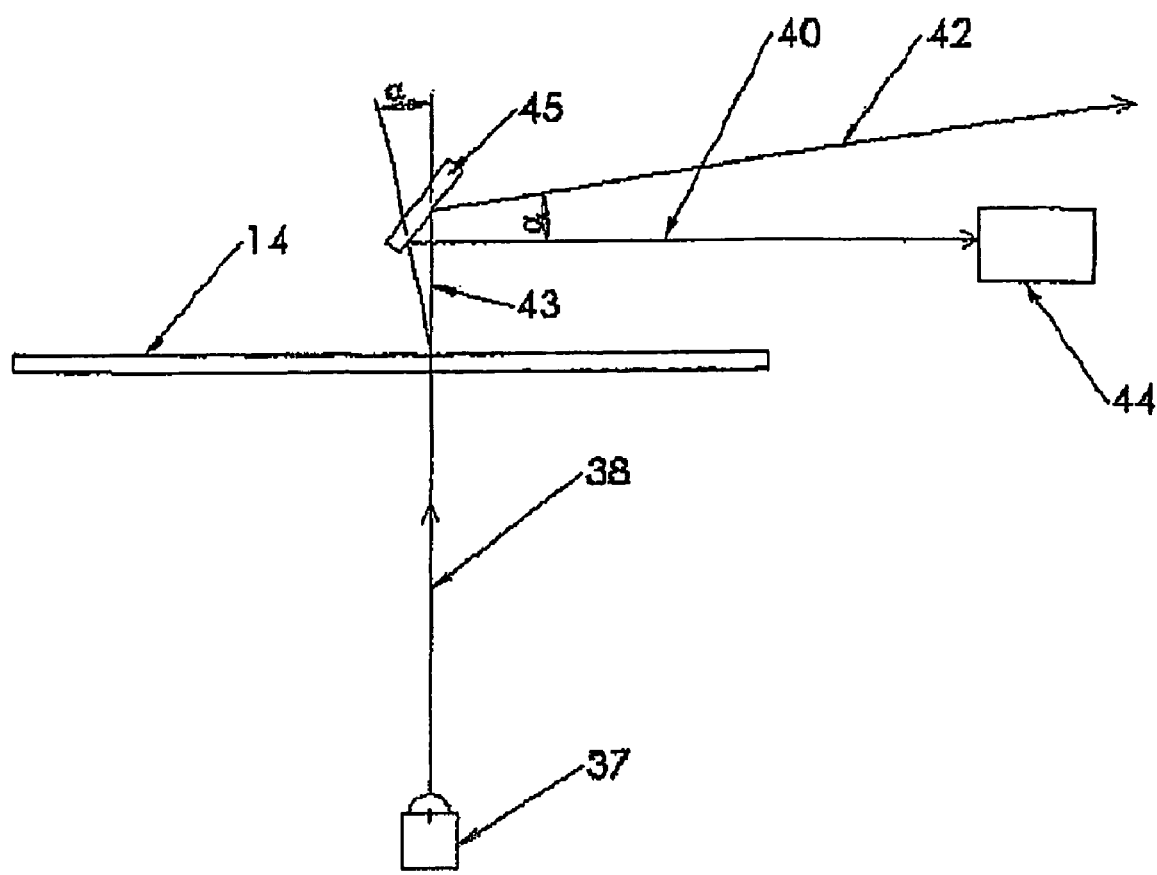
FIG. 4 is a schematic drawing illustrating the optical geometry in the imaging device of FIG. 2.

In FIG. 4, a schematic drawing is shown illustrating the optical geometry in an example embodiment. The beam 38 emitted from the LED array 37 is incident on the slide 14. One portion 40 of the beam 38 containing rays deflected at binding partners (not shown) bound on the slide 14 emerges as a deflected portion 40 after the slide 14, at an angle $\alpha$ to an undeflected portion 43. This angle $\alpha$ is typically in the range of 3-5°, and may be empirically determined by adjustment of the mirror. Accordingly, through suitable orientation of the mirror 45, it can be ensured that substantially only the diffracted/deflected or offset planar portion 40 is directed towards the line scan camera 44, and the undeflected portion is reflected away from the camera, as is shown at 42. It will be appreciated by the person skilled in the art that at least one other portion (not shown) of the initial beam containing light rays deflected or diffracted at binding partners (not shown) bound on the slide 14 is expected to emerge after the slide 14, at an angle ($-\alpha$) to the undeflected portion 43. The other diffracted/deflected or offset portion or portions may collectively, alternatively, or additionally he directed towards the line scan camera 44 in different embodiments using a suitable reflecting arrangement or through optical variation in the field of view of the camera 44.

Figures 7, 8:
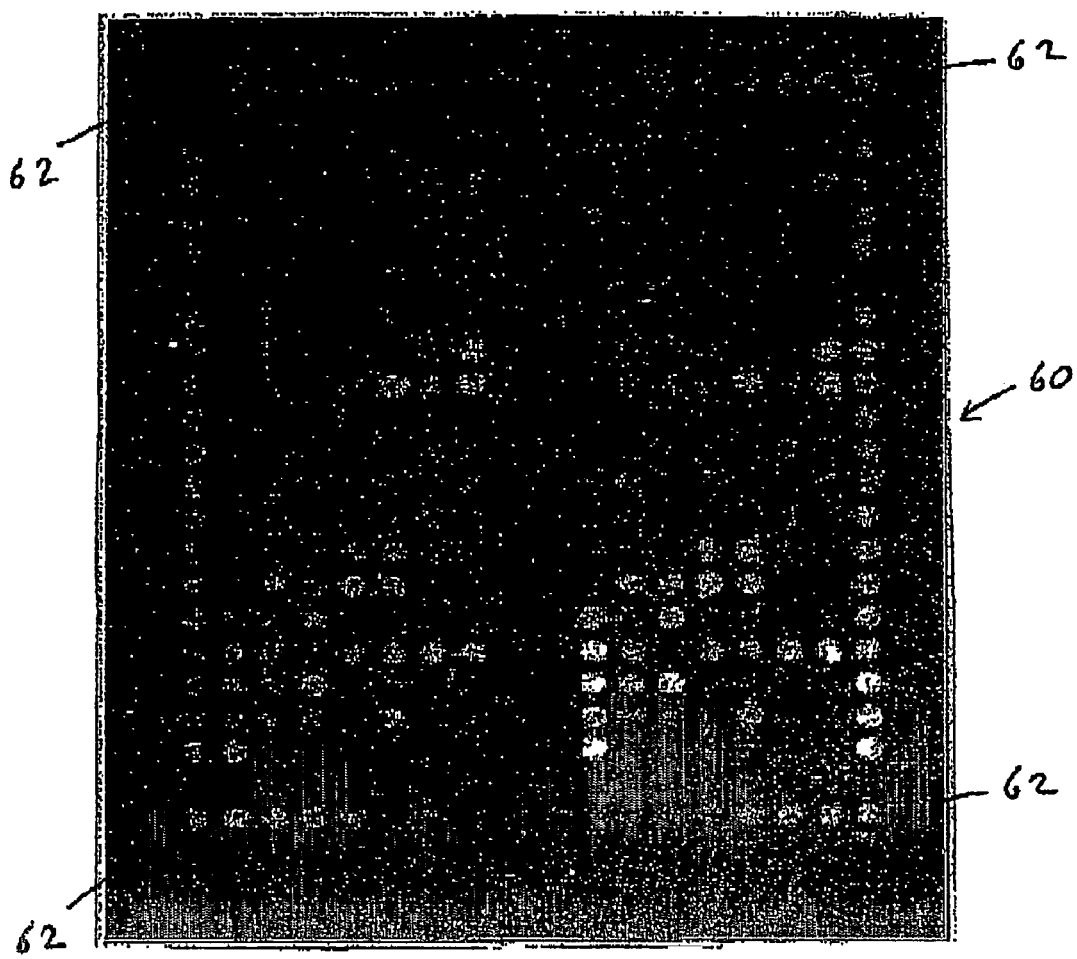
FIG. 7 shows an image taken of a sample slide utilising a prototype imaging device embodying the present invention.
FIG. 8 shows a data array illustrating the information from a sample slide to be passed to a pattern-matching program, embodying the present invention.

It has been recognised by the applicant that the utilisation of substantially only rays that have been diffracted at or otherwise deflected as a result of binding partners bound on the sample slide 14 enables the capturing of a positive image of the bound array. In other words, the number of cells or bound partners in individual sections of the sample slide 14 is proportional to the light intensity in the captured image, thereby giving rise to a dark field image. Furthermore, it will be appreciated that capturing of a positive image avoids problems associated with a high background intensity of a transmitted portion of the illuminating beam. FIG. 7 shows an example image 60, which will be described in more detail below.

Figure 5:
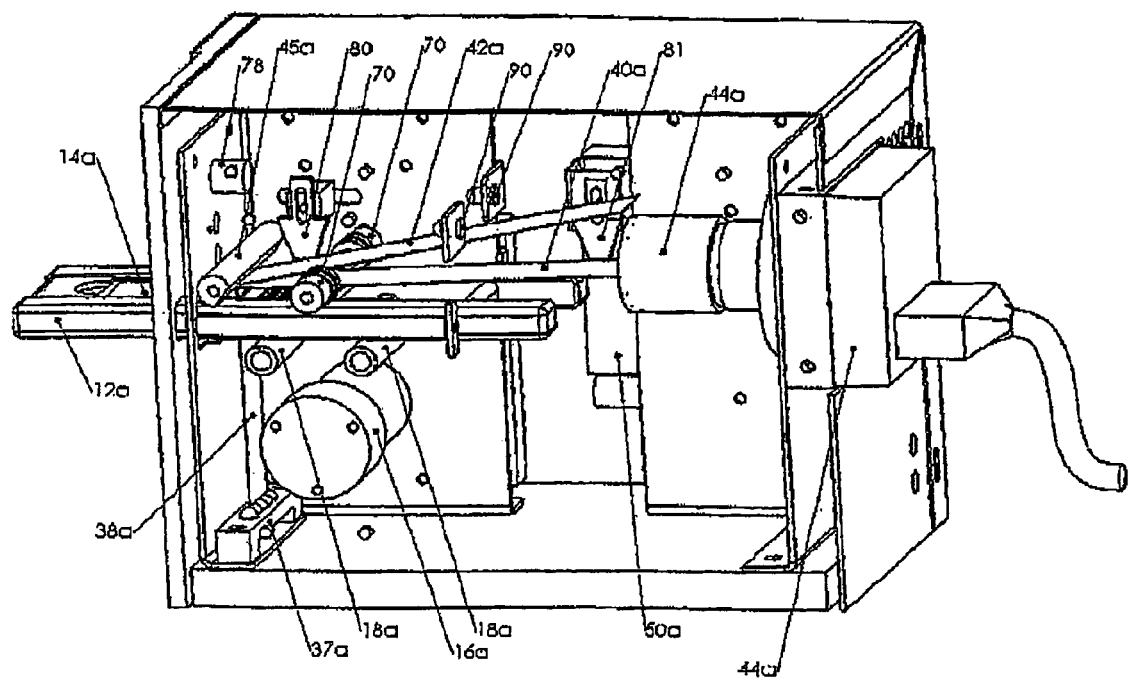
FIG. 5 is a schematic perspective drawing illustrating a second preferred embodiment of an imaging device of the present invention.
Figure 5A:
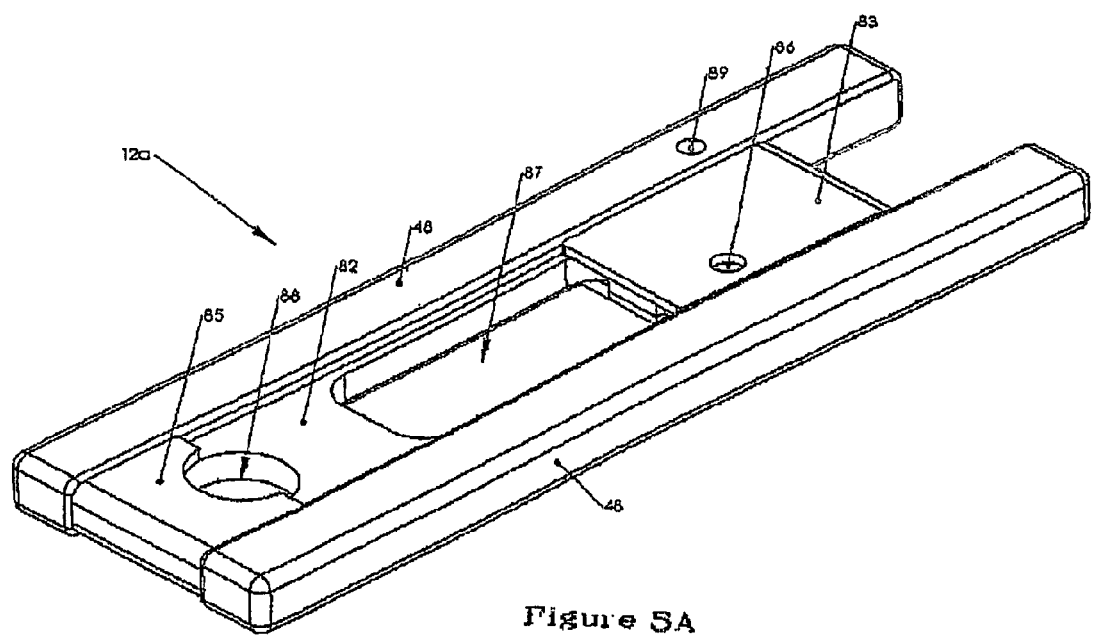
FIG. 5A is a top perspective view of a slide tray assembly forming part of the imaging device of FIG. 5.

Referring now to FIGS. 5 and 5A, a second preferred embodiment of an imaging device 46 is shown in which components which are similar or identical to those in the first embodiment have been numbered accordingly, and suffixed by an "a". A carriage or slide tray 12a carries a sample slide 14a for analysis of the bound array 102 mounted on the slide. An LED light source including an LED bracket 37a carrying a linear cluster of LED's emits a narrow beam of light 38a which is directed towards the underside of the slide. In the particular embodiment, a linear cluster of five LED's is used having a blue emission wavelength of 490 nm to illuminate a band on the slide having a width or about 10 mm. A mirror 45a directs the portion 40a of the initial light beam containing rays which have been diffracted or otherwise deflected at bound binding parser in the array towards a line scan capable digital camera device 44a. In the embodiment, a Basler L101K line scan camera is used.

A slide tray 12a which includes a pair of drive tracks 48 is moved to and fro by means of a pair of drive rollers 18a and idler rollers 70 which are rotated using a DC motor 16a. A push button 78 is pressed to present the slide tray 12a for insertion of the sample slide. The sample slide is inserted into a recess 82 within the slide tray 12a, with the leading edge of the slide pushing up against a sprung loaded slide retainer 83, and the trailing edge of the slide abutting against a slide stop 85. A slide sensor indicates the presence of the slide by sensing a obturation in the cutout 86 as it is displaced by the slide. A window 87 allows the light beam 38a to illuminate the underside of the slide, and finger aperture 88 enables the slide to be readily removed and replaced.

A slide sensor 89 senses when a slide has been inserted and signals a controller 50ato commence acquisition. The motor 16a advances the slide tray 14a at a speed sufficient for the line scan camera 44a to take successive linear images of the light diffracted or otherwise deflected by the bound cells on the slide it is moved across the band of light 38a emitted from the light source 37a. The line scan camera 44a has a linear array of sensors having a width of one pixel and a length of 1,024 pixels. In the present embodiment, this equates to a linear image having a length of 25 mm and a width of 0.025 mm. As a result, as the slide tray is moved forwards, a successive series of linear images of the bound cell array are scanned by the line scan camera 44*a*. It is clear from FIG. 5 how non-diffracted or non-deflected light 42 plays no role in the formation of the image as it is reflected away from the linear aperture of the line scan camera. As the bar code 124 on the slide reaches the imaging region, this is sensed by a microswitch (not shown) as a result of which the light source 37*a* is turned off and the light source 90 is turned on to illuminate the slide bar code, thereby allowing the bar code 124 to be included in the image. A proximity sensor 81 detects the presence of the slide tray and signals the programmable logic controller (PLC) 50*a* to reverse the drive motor to enable removal of the sample slide 14*a*. If detection of fluorescence via fluorochromes is required, the light source 37*a* is turned back on. Full extension of the slide tray is detected by a proximity sensor 80 sensing a sensor target 89 on the slide tray, and signaling the controller to turn the drive motor 16*a* off.

Figure 6:
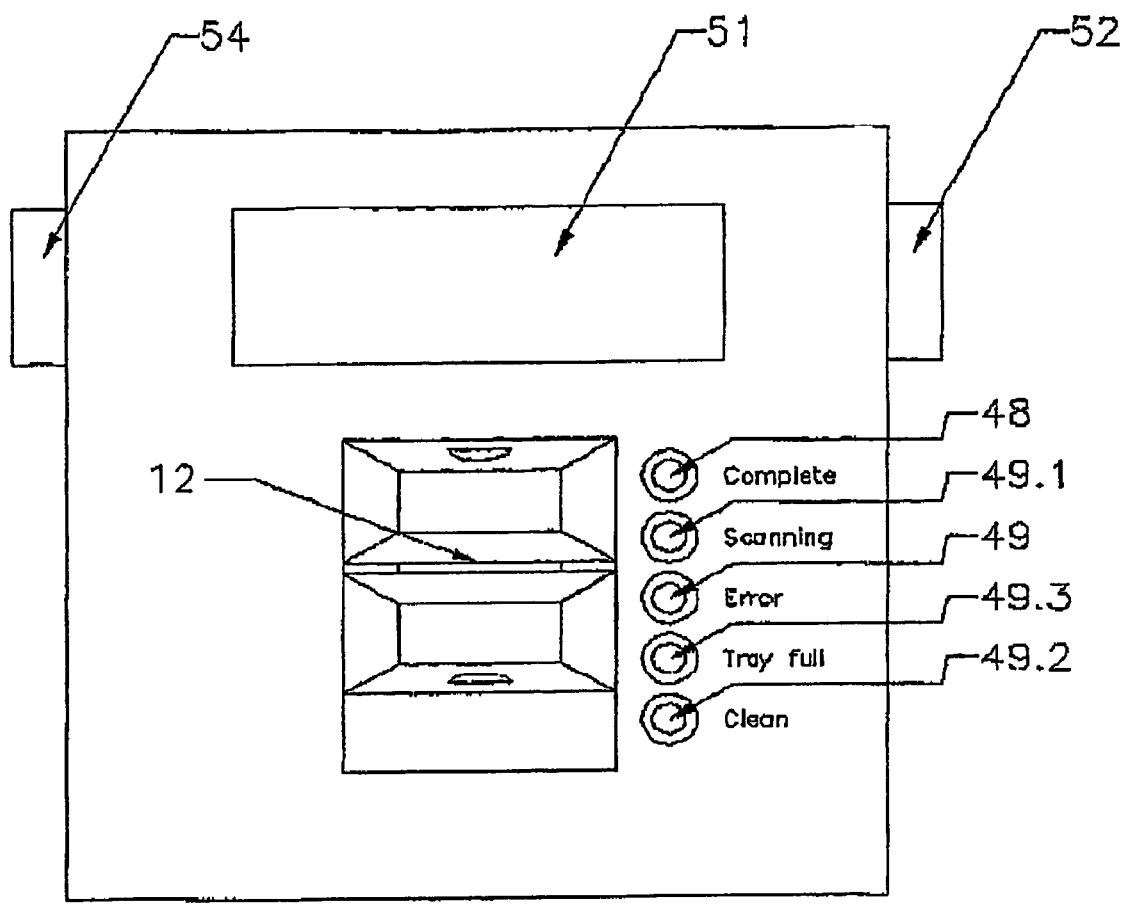
FIG. 6 is a schematic drawing of a front view of the imaging device of FIGS. 1 and 5.
Figure 6A:
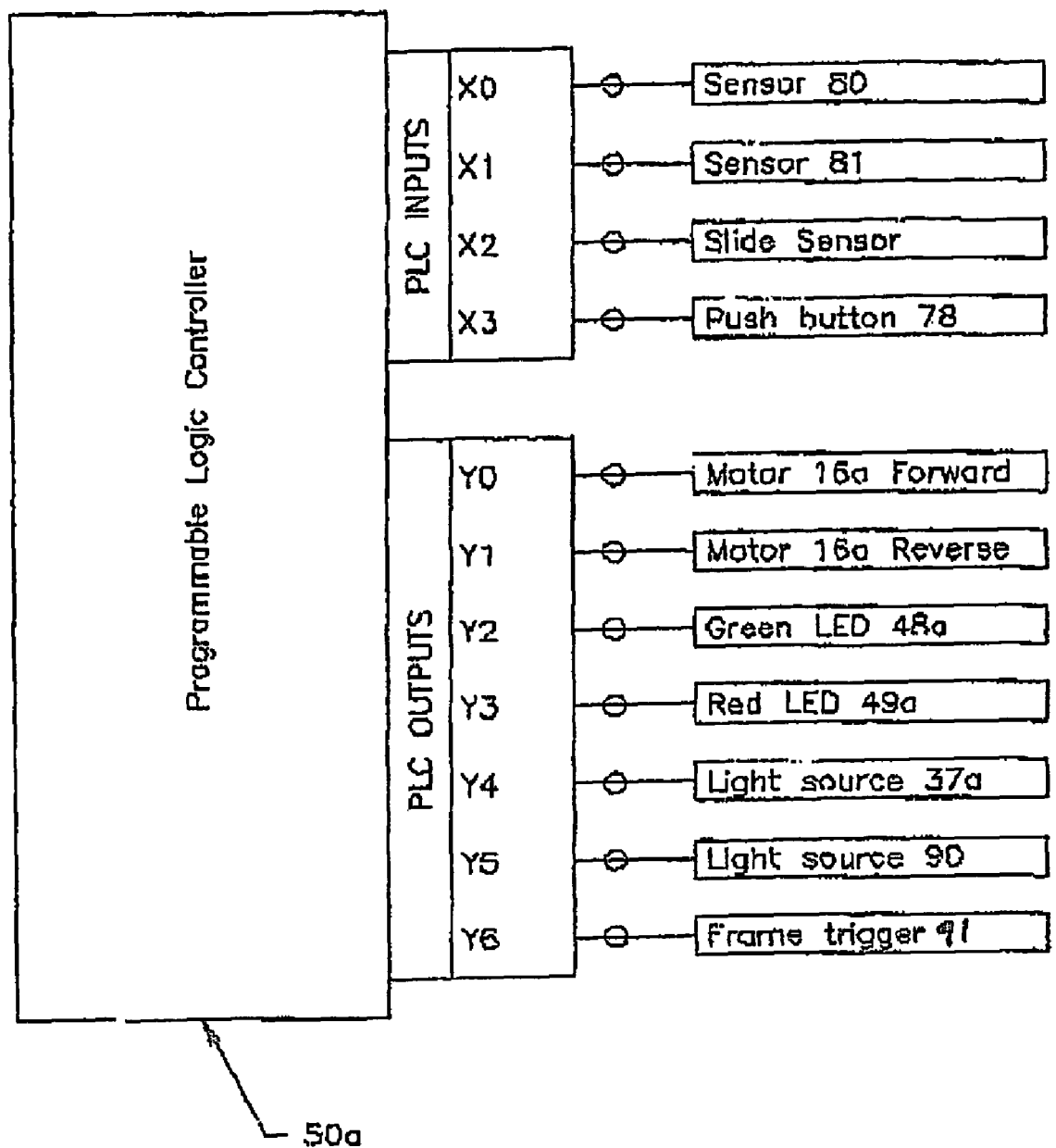
FIG. 6A is a functional block diagram of the imaging device of FIG. 5.

In FIG. 6A, a PLC 50*a* which controls the operation of the imaging device 46 is shown having as inputs the proximity sensors 80 and 81 and slide sensor 89, together with push button 78. The PLC outputs includes motor forward and reverse outputs for the DC motor 16*a*, and LED outputs 48*a* and 49*a* for indicating scanning and error events respectively. Also included are outputs for controlling the operation of the respective primary and bar code illuminating light sources 37*a* and 90, and a frame trigger output 91.

The basic principles of operation of the example imaging devices 10 and 46 embodying the present invention are as follows, with reference to FIGS. 1, 2, 5 and 6:

Developed slides 14 are inserted into the slide carriage 12 and 12A in a horizontal orientation.

The slides 14 are transported through the planar light beam 38 to obtain a series of linear images.

If the slide 14 has been sequentially scanned successfully, an LED 48 (FIG. 6) will indicate the scan is complete. If not, an error indicator 49 and optional audible alarm will be activated. Diagnostic tips will be displayed on an liquid crystal display (LCD) display 51 of the machine or a connected PC. Additional indicators include scanning LED 49.1, "tray full" LED 49.2 for indicating a full drip tray, and "clean" LED 49.2 indicating when the imaging device requires cleaning.

The slide 14 is ejected from the machine and removed.

The linear images are processed in the processing unit 50 (FIG. 2) or an external PC-based frame grabbing card and results made available to the LCD Display 51 (FIG. 6), a serial port 52, and/or an Ethernet port 54, or the PC monitor.

In the example embodiment, the bound binding partners are made visible by transmitting light through the slide and viewing the light diffracted or otherwise deflected at an offset planar orientation by the binding events. The image 60 shown in FIG. 7 is assembled sequentially from a series of linear-images taken using a prototype of the example embodiment Although the image 60 is relatively coarse, a person skilled in the art will appreciate that there is sufficient information to interpret a result. It is expected that a much cleaner image can be captured by production scanners embodying the present invention.

In the prototype of the example embodiment, the cells are visible through a narrow band across the slide (approximately 2 mm). The slide is moved with respect to the light source and camera, with a thin (0.025 mm) slice of image taken for each movement, and then reassembled in the processing unit 50, which may form part of the camera. Alternatively, the camera communicates with a frame grabber card in a host computer via a camera link or data communication cable. Image acquisition and processing is performed using appropriate in the computer-base software.

In the following, some further aspects of example embodiments of the present invention are discussed.

Image Normalisation and Processing:

Images from scanner to scanner and across time will differ for the same patient sample due to variation/degradation in the light source, imaging device, slide's biology and other environmental conditions. The use of reference binding partners such as e.g. monoclonal antibodies (Mab's) 62 (FIG. 7) in at least the four corners of each array and other outer peripheral regions of the array can be used to normalise the image by:

Indicating the biological condition of the slide;

setting an upper limit for the intensity of each dot and by measuring the background around the array, an intensity range can be set from zero to maximum cell binding, and the results scaled accordingly. This will se any variation/degradation in the system(s);

defining the spatial boundaries for binding partners, and once found, for pattern recognition of said binding partners The Mab's 62 man also help locate the dots on each array. Once the corners of each array are identified, a virtual grid can be overlayed on the image, locating or other non-reference binding partners. The background can then be removed and the image enhanced using techniques known to those skilled in the art. The average intensity of each square in the grid can then be used to quantify the cell binding on each dot in the array. A quantification of the resulting scale from e.g. 0-100 or equivalent pixel intensity has been easily achieved. It is expected that quantification levels well in excess of this should be achievable. It will be appreciated by the person skilled in the art, that more reference binding partners, or indeed fewer, could be used in different embodiments, depending on specific processing requirements. Such processing can be completed either locally or remotely from the camera and either immediately after image capture or at a later time in the future.

FIG. 8 shows a matrix illustrating the digital information that may he obtained from an array for passing on to a pattern-recognition program used to identify a molecular profile.

The following model outlines the example interaction between a scanner embodying the present invention and other devices it communicates with.

The device is preferably able to communicate with:

External or internal computers and printers, e.g. pathology computers and printers, and may need to comply with existing data communication standards and protocols.

A reference database.

In the following, examples of other processes preceding and following the utilisation of a scanner embodying the present invention will be briefly outlined for an example implementation.

Processes Preceding the Scanner:

By way of example, the slides are developed by transferring the samples, to the slide and allowing it to incubate, then washing the slide in phosphor buffered saline (PBS) twice, with or without chemical agents to access intracellular protein compartments and with or without fluorescently active molecules e.g. fluorochrome markers (refer to different example sample type described below with reference to FIG. 8), fixing in fomaldehyde and then washing in PBS two or more times.

Processes Following the Scanner:

The slide will be disposed of in biological waste.

The Scanner is Preferably Designed with Suitable Materials and Features to Enable:

External cleaning with a mild detergent.

Not to allow contamination of the slide (biological and other).

Allow slide receptacle to be cleaned, sterilized and drained of any fluids that may spill from the slide.

Accept a standard glass slide format or equivalent and sustain in excess of 500,000 operation cycles.

Figure 9:
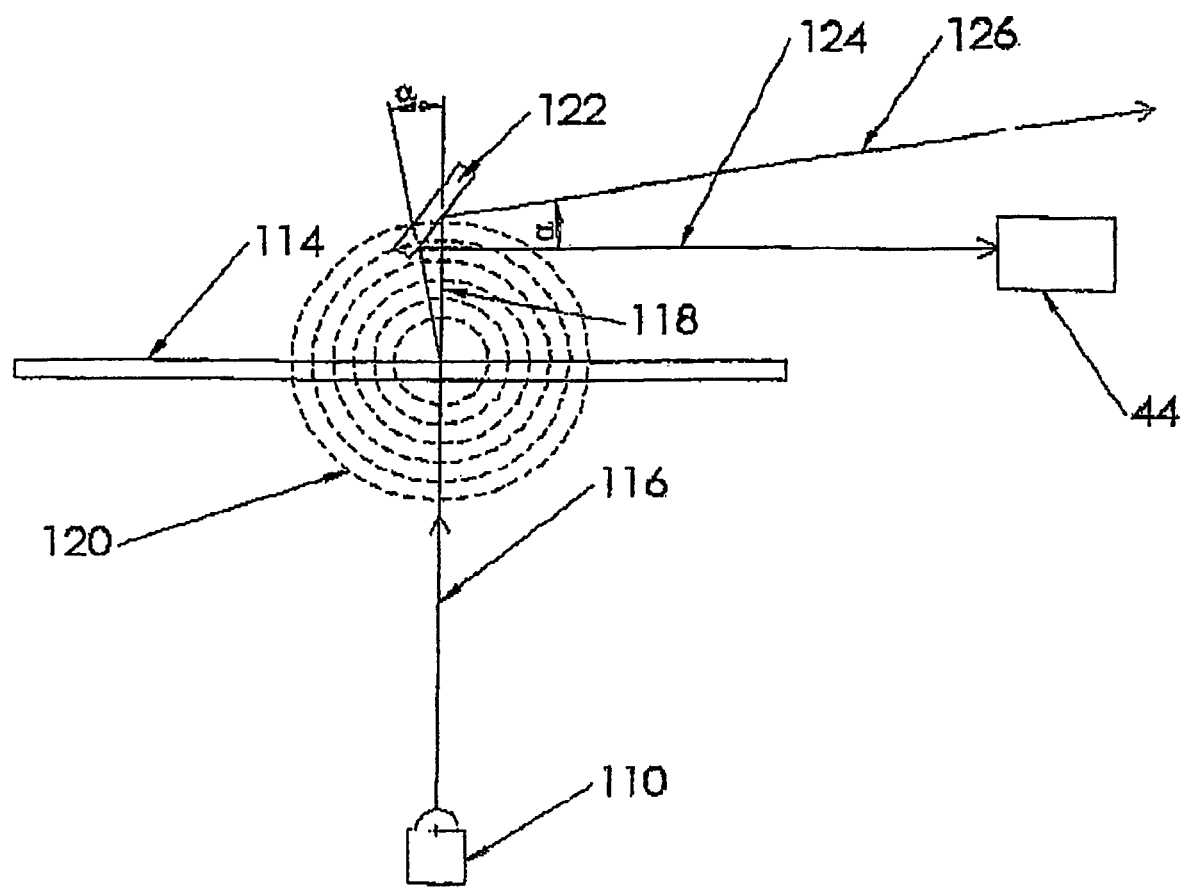
FIG. 9 is a schematic drawing illustrating the optical geometry in the imaging device of FIGS. 1 and 3, for a different sample type.

FIG. 9 is a schematic drawing illustrating the optical geometry in an imaging device embodying the present invention, for the operation of dual detection modalities. In this embodiment, a substantially flat beam 116 is emitted from an LED light source 110, capable of variable wavelength emissions towards the underside of a sample slide 114. As described above with reference to FIG. 4, a narrow portion of the light beam 116 is transmitted through the slide 114 and emerges as a transmitted portion 118 from the top of the sample slide 114.

In the configuration described in FIG. 9, the sample slide 114 contains samples in which fluorescent markers have been utilised to identify the presence of a particular molecule, such as e.g. a protein, in the samples of binding partners. The narrow beam light source 110 is chosen in this embodiment to contain within its spectrum a wavelength suitable for exciting the fluorescent markers and resulting emission of light from the fluorescent markers. As illustrated in FIG. 9, the light emitted from the fluorescent markers may be regarded as originating from a point source, thus yielding an omnidirectional light emission field 120, creating the series of linear images for subsequent reconstruction.

Accordingly, by way of a mirror element 122, a portion of the omnidirectional fluorescent light emission, indicated as arrow 124, is directed towards a digital camera device in the form of a line scanner camera capable of monochromic and polychromic detection 126, such as a Basler L301KL. Through appropriate selection of the angular position of the mirror 122, it can be ensured that the transmitted portion 118 of the illuminating light beam 116 is reflected at the mirror element 122 away from the line scanner camera as is shown at 126, i.e. the "collection" angle is offset relative to the transmitted beam portion 118.

The optical diffraction/deflection and fluorescent detection, both requiring reconstruction of linear images, are directed towards the line scan camera either concurrently or alternatively for each image. Dual detection modalities are best utilised when the wavelength of light illuminating from the flat light source approximates to the excitation wavelength of the fluorescently active molecule or molecules. In yet another embodiment, multiplexing of different fluorescently active molecules occurs after direction of planar and or offset planar images to the camera system, either in an alternative or simultaneous operational mode, dependent on the polychromatic detection capability of camera.

In one embodiment of the invention, the line scan colour camera is arranged to detect diffracted or otherwise deflected light during a forward pass of the slide and fluorescent emissions of light during a reverse pass of the slide as it is ejected from the device. The camera accordingly operates in a monochromic detection mode on the forward pass and converts to polychromic detection mode during the reverse pass. On the return pass the slide travels at a slower speed, allowing for greater exposure time to detect the weaker signal emitted from the fluorochromes. Suitable band pass filter sets, such as Omega filters supplied by Omega Optical, Inc., and Chroma filters supplied by Chroma Technology Corp., may be used to ensure that the correct wavelength for stimulating excitation and emission peaks in respect of the selected dye/nucleic acid complex is used. Preferably though, the wavelength of light is selected such that detectable excitation is achieved without the need for filters, and using software-regulated discrimination. In the present case, the blue LED arrangement is chosen as being suitable for the celltracker green fluorochrome. It will be appreciated that bi-colour or tri-colour LED's may be used to provide a broader range of wavelengths capable of exciting more fluorochromes. Image reconstruction establishing each binding event is based on one or more digital images derived from each detection mode.

Figure 10:
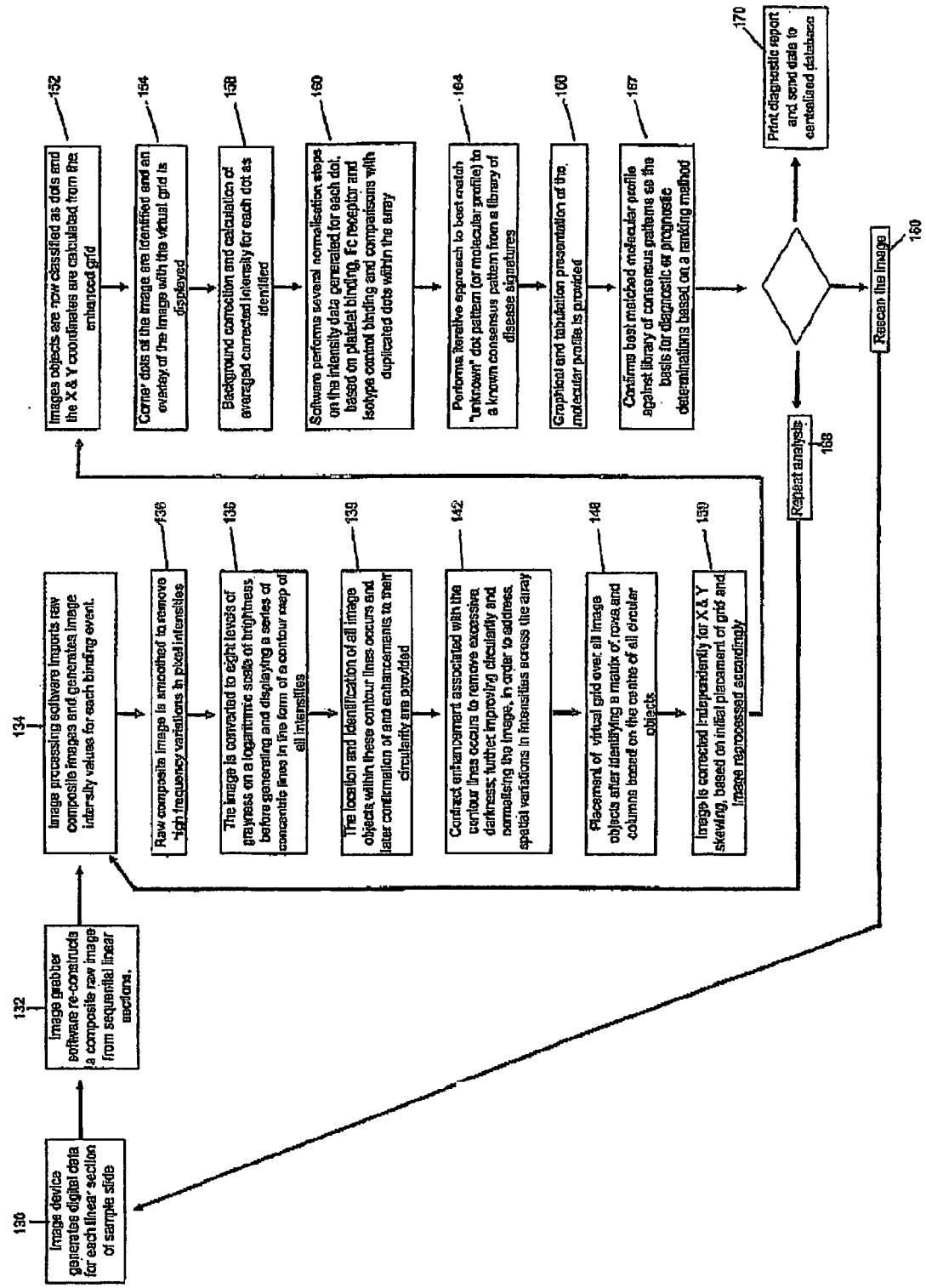
FIG. 10 is a flow chart showing the steps involved in deriving and processing an image in an embodiment of an image deriving and processing method of the invention.

The image normalising and processing procedure referred to previously with reference to FIGS. 7 and 8 will now be described in more detail with reference to the flow chart of FIG. 10 and the accompanying images. The imaging device 10 or 46 generates digital data in the manner previously described, as shown as 130. Image grabber software in a frame grabber card forming part of the camera or an external microprocessor constructs a composite raw image (FIG. 8) from the sequential linear sections, as is shown at 132. Image processing software imports the raw composite image, as shown at 134, to generate image intensity values for each binding event.

The image processing methodology include smoothing the composite image to remove high frequency variations in pixel intensitics 136 and then converting the image to eight levels of greyness on a logarithmic scale of brightness before generating and displaying a series of concentric lines in the form of a contour map of all intensities, as shown at step 138. Smoothing removes high frequency information from the image that can make contour lines jagged and leave gaps. The image is converted to eight levels of grey on a logarithmic scale of brightness is formed using a 256 bit look up table set to convert all image brightness levels to the following values, namely 1, 2, 4, 8, 16, 32, 64 and 128. The image pixel brightness values used as an index to look up this array. The boundaries between the different grey levels are used to use to create the contour lines.

Figure 10A:
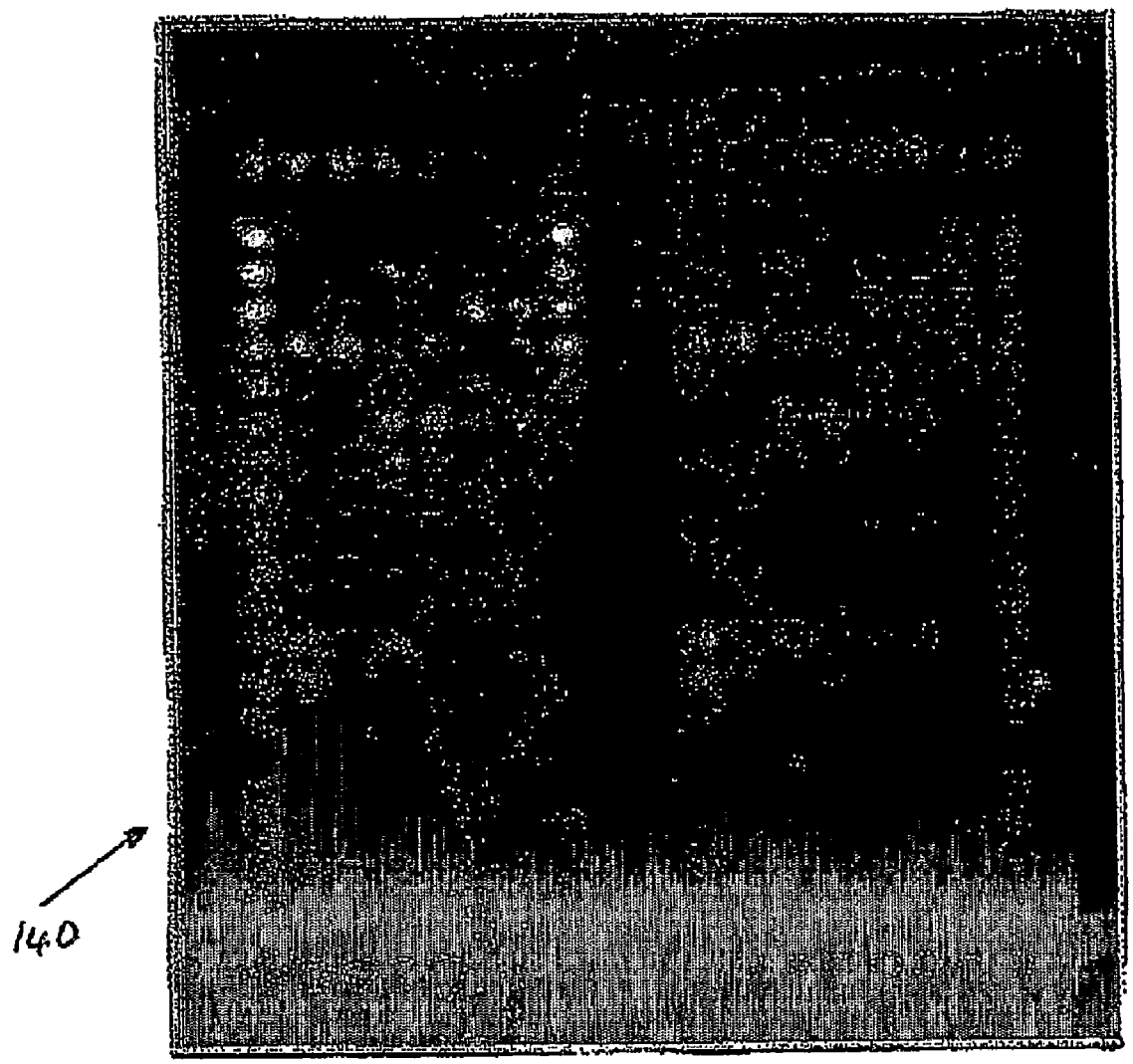
FIG. 10A shows a step in the imaging processing method of the invention in which the image is smooth and contoured.

The contour map is composed of a background of maximum-intensity pixels, i.e. white pixels having a value of 255. The process traverses the image by visiting every pixel element inside x and y loops. That clement is treated as the centre of its eight surrounding pixels. If the program finds a centre pixel with any pixel of the eight that is brighter than it, it marks that centre pixel as being on a contour. The marking is done by copying the pixel value (holding only one of the values 1,2,4,8,16,32,64,128) to the second array to hold only the pixels of the contour lines of the image. The result is an array of the same dimensions as the image, with all pixels set to 255, except for pixels on contour lines holding the grey values of the outer edges of regions which are darker than their neighbours. A typical contour map derived from the image of FIG. 7 is shown at 140 in FIG. 10A.

The location and identification of all image objects within the contour lines occurs and the confirmation of and enhancements to the circularity are provided, as shown at step 139. In a subsequent normalisation step 142, image enhancement associated with the contour lines occurs to remove excessive darkness, thereby further improving circularity and normalising the image in order to address spatial variations and intensities across the array. In particular, each separate contour line resulting from the above process is now classified as a separate image object. As each contour line is classified, its pixels are added to an "Already processed" array with the same dimensions as the image. This allows rapid identification as to whether a given contour line has already been processed or not, by looking up any pixel of the line. The coordinates of the pixel are used to access the corresponding element in the "Already processed" array, which was previously cleared.

Every pixel of the contour map array is scanned by an x and y for loops. If a pixel is found to be a member of a new (unprocessed) contour, its coordinates are passed to the ImageObjectPixelsFind method, which finds the rest of the pixels on the contour line and classifies the contour as open or closed.

The method finds all the pixels of the contour line and flags each one as "Already Processed" in the "Already Processed" array. It also returns two other arrays, RegionX( ) and RegionY( ) that hold the corresponding X and Y coordinates of each pixel in the contour line. These two arrays essentially list all the pixels in the contour line. The pixel coordinates contained in these two arrays are then copied to an array of image objects (ie contour lines) which holds a list of all the pixels in each image object, as well as the number of pixels in the object, and the grey scale brightness of that object (i.e. of the contour line which contains a grey scale region of that logarithmic grey-scale brightness).

The result is that each image object (represented by a contour line) is identified and listed in the ImageObject( ) array, and can be rapidly traversed by processing each pixel in the list of pixels for that object. If the number of circular objects with contours of more than 45 pixels is less than 10 then the image is rejected with the message:

"This image is too poor to process. (Not enough recognisable dots). Perhaps the slide has dried out? Please re-wet and scan again or re-process."

Image objects are then classified as being circular or not. The classification is performed by a method, that analyses a single image object. This routine is called in a loop which processes every object on the image. A routine is used to calculate the length of the contour line of the object and whether is a closed or open object. Closed means the contour is a loop. Open means it is a line whose end points do not coincide. Each object has a contiguous contour line. The routine also uses an ImageObjectCenter to find the position of the centre of any closed object, and also its diameter in the X and Y directions. Using the circumference of the object and its diameter information, the routine then classifies the object as circular or not.

The result is that certain image objects are now classified as circular. These are candidates for the contours of dots on the array. The centres of many of these objects will coincide with the centres of dots on the array. The process of locating these objects and their centres breaks the back of the task of locating the array somewhere on the image, and allows the virtual grid to be accurately aligned over it.

The image enhancement routine enhance the image to show only the range of brightness that contains significant information. This will enhance the contrast of the informational parts of the image by removing very dark areas that carry very little information. This will make it easier to detect circular regions indicating dots, and also tends to normalize the image somewhat to enhance diagnostic accuracy.

One way to discover which brightness levels contain information is to look for the first logarithmic brightness level that contains any circular regions (starting at the darkest level). Contour brightness runs from 1 to 128 in eight steps, doubling in brightness every time. The first level containing at least one suitable circular object is labelled as level n. Then the image is reprocessed to show only the information between the Brightness B of level n-1 ($B_{n-1}$) and 255. This is done by applying the following formula to each pixel of the image to produce the pixels of the new enhanced contrast image:

$$PixelValue(x,y)_{new} = Max(0, (255*(PixelValue(x,y)_{old} - B_{n-L})/(255 - B_{n-1}))))$$

for all pixel coordinates x,y of the image

Where the Max( ) function simply ensures that no new pixels have a negative brightness value.

Figure 10B:
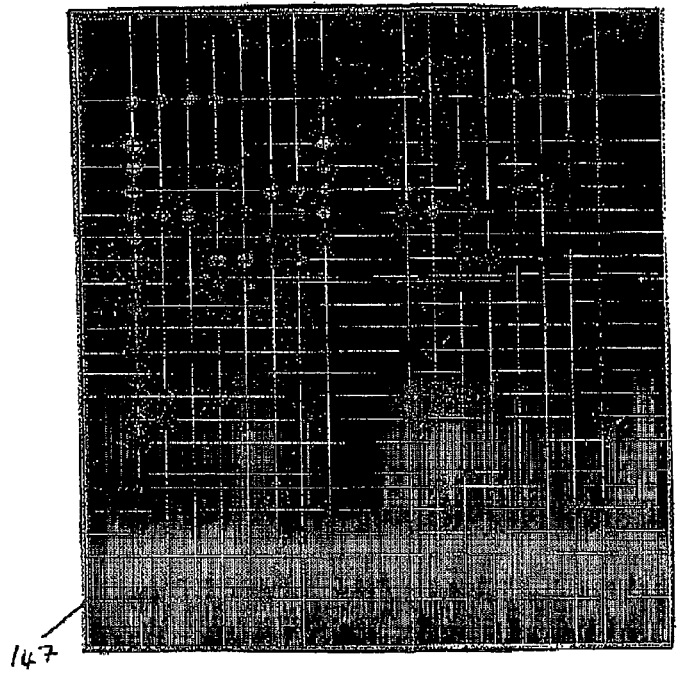
FIG. 10B shows a further processing step in which a virtual grid is arranged to overlay the image.

The new enhanced image is then completely reprocessed in a second phase to obtain a new set of contour objects. This includes completely regenerating the 8 level brightness regions and the contour objects and reclassifying them. However, this enhancement process is obviously omitted from the second phase of processing. This step is shown at 146, initial placing of a virtual grid 147 over the image, as is shown in FIG. 10B.

To find the columns of the array, a single histogram is drawn across the image of the number of circular objects with a x-coordinate falling into each histogram cell. Histogram cells are one pixel wide. The histogram continues right across the width of the image. When finding columns, the y-coordinate of the circular object is ignored. (A similar process is used to find rows, but this time, the histogram is drawn down the array, and the use of x and y-coordinates is reversed.) If the dots fall into columns, the histogram will show a peak for each column.

By looking at the peaks and finding the best integral column separation the location of each column on the grid can be identified, unless there are simply too few dots in the image to make this possible. The histogram requires some smoothing, to allow reliable detection of its peaks.

If the peaks of the histograms are smeared, or they have closely-spaced dual peaks, the slide image is probably skewed. To aid algorithm evaluation, testing and debugging, it may help to draw the histograms as an overlay of the image. As a result, the position of at least some of the rows and columns of the array are known, and the column separation and row separation can be established, allowing a length conversion scale to be developed between the array design and the array image.

Each image object is allocated to one of the identified grid rows if possible. Any image object flagged as circular and lying on a valid column is allocated to one of the rows found providing it falls within specified limits.

Due to various factors, it has been found that it is not safe to assume that the row skew is the same as the column skew, in other words the skew may not be all due to image rotation, some may be due to other forms of image distortion. Thus vertical and horizontal skew is removed separately. However, skew is assumed to be linear and any higher order distortions are not corrected.

For each grid column found, the slope of that column is identified by fitting a straight line to the x,y coordinates of the image objects flagged as falling in that column. This fitting is performed using the standard least-squares method. The slope of all the columns is averaged to find the average vertical skew for the image. The de-skewing step is illustrated at 150 in the flow chart. Row skew is found and corrected by an analogous method.

Once the image has been de-skewed, image analysis is repeated once more on the enhanced de-skewed image, recreating image areas and contour lines, and re-classifying the image objects. Obviously the enhancement and de-skewing processes are skipped for this third phase.

Those circular image objects falling on column row intersections within reasonable boundaries are classified as dots. Other image objects are not classified as dots and are ignored for the following process.

The previously generated row and column separations are used to generate approximate X and Y scales (which may well be quite different). These scales can then be used to convert image pixels to mm and vice versa so dimensions in the slide definition can be related to dimensions on array part of the image, is indicated at step 152 in the flow diagram.

The first and last columns of the slide are used to locate the array definition over that part of the image holding the array. The X co-ordinates are known from the first and last columns of the array, from which can be worked out the co-ordinates of the remaining interior columns.

An overlay of the image with the virtual grid is displayed, as is indicated at FIG. 10B. The centres of the co-ordinates are located by finding the nearest image data to each plan corner dot. The enhanced de-skewed image is overlayed to the operator with the deduced corner dot circled. The operator then has the option to locate the corner dot, in the event of the corner dot location failing for poor quality images. Once the operator has clicked the final dot, the locations are used to allow the slide plan over the image of the array.

Using the new corner dot positions it is possible to calculate a more accurate conversion scale between images pixels and mm. This allows the virtual grid representing the plan of the array area of the slide to be accurately located over the image of the array, so each dot appears centred in its own grid square.

The new x and y-scales to convert from pixels to mm are calculated by comparing the distances the x-y co-ordinates of the centres of the four corner dots in pixels in the appropriate direction, against the mm distance of these dots on the array plan derived from the Slide Definition.

The row case is harder because the top and bottom rows of the array are less distinctive than the left and right columns, holding progressively diluted antibody subtypes that do not all show clearly on the image. Additionally, a complete top or bottom row may be almost obscured by fluid, spurious light from fluid edges and waves, and/or progressive drying out of the slide starting at the top or bottom, and not all rows may have been identified in the earlier processes, since some rows may have almost no dots visible.

Thus a different algorithm is used to align the slide plan over the image in a vertical direction. Firstly row separations are converted to mm using the approximate scale derived above. Then the slide design is conceptually slid vertically up and down the image, looking for the best match between (a) circular image objects recognised as left and right edge dots and (b) the edge dots on the plan. This is done in an iteratively in a single pass by conceptually moving the plan down the slide image one pixel at a time, and summing the total distance between each image dot and it's nearest neighbour on the plan. The shortest such distance, and its pixel index is recorded during the iteration. When the iteration is complete, this particular location is the best guess for aligning the slide design over the image of the array.

If a dot read error is detected, data entered remains on the screen, and the operator has to the option to rescan the image, as is shown at 180.

Figure 10C:
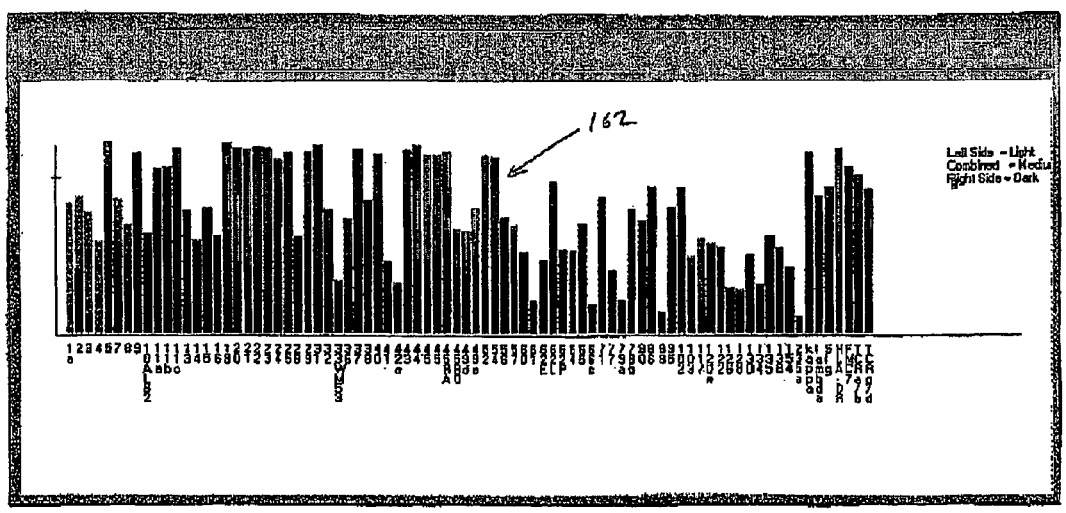
FIG. 10C shows a histogram illustrating average intensities representative of binding events in the diagnostic marker arrays in the processed image of FIG. 10B.

At step 158, background correction calculated using averaged corrected intensity for each dot as identified is performed. Intensity values are read off one by one. As is shown in FIG. 10C, a histogram 162 is formed of the image intensity from 0 to 255 of every pixel in the grid square locator containing the dot. The local background intensity is found and defined as the pixel brightness level M. M divides the pixels in the region into two sets, namely a dimmer set comprising all the pixels which are dimmer or equal in brightness to M, and a brighter set B comprising all the pixels in the set that are brighter than M. The number of pixels in set A bears a pre-set ratio to the number of pixels in set B and is typically 50%.

Having determined which pixels are part of the local background (above), it is now easy to calculate the relative brightness of each dot.

The process starts by summing the image intensities of all the pixels inside the dot region, based on its calculated radius. The algorithm also includes consideration of pixels that lie partly inside the dot radius, accumulating a fractional part pro-rata according to the fraction of the pixel lying inside the dot. The number summed (Delta) is the pixel brightness less the local background brightness calculated above.

The average value of this sum per pixel (InnerAverageValue) is then calculated by dividing the sum by the total number of pixels inside the dot, including fractional parts.

The Dot value is then formed by taking the InnerAverageValue and normalizing it to represent it as a ratio against the maximum possible brightness above the local background.

As indicated at step 164, once the dot values have been identified and incorporated in a matrix such as that illustrated in FIG. 8, the software performs an iterative approach to best match unknown dot patterns or molecular profiles to a known consensus pattern from a library of disease signatures. Graphical and tabulation presentation of a molecular profile is provided at 166, and the best matched molecular profile is confirmed against the library of consensus patterns as the basis for diagnostic or prognostic determinations based on a ranking method. The analysis may be repeated at 168 if unsatisfactory, or the image may be rescanned at 180. Once a matched molecular profile has been obtained, a diagnostic report is printed and the data is sent to a centralised database, as is shown at 170.

It will be appreciated by the person skilled in the art that numerous modifications and/or variations may be made to the present invention as shown in the specific embodiments without departing from the spirit or scope of the invention as broadly described. The present embodiments are, therefore, to be considered in all respects to be illustrative and not restrictive.

For example, while certain example sample materials have been described, it will be appreciated that the present invention is not limited to the analysis of particular sample materials. Furthermore, it will be appreciated that the present invention is not limited to use in diagnostic or prognostic applications.

In the claims that follow and in the summary of the invention, except where the context requires otherwise due to express language or necessary implication the word "comprising" is used in the sense of "including", i.e. the features specified may be associated with further features in various embodiments of the invention.

The invention claimed is:

1. An imaging device comprising:
   a carrier stage for carrying a sample slide,
   a light source for illuminating the sample slide, said sample slide including an array of samples,
   a drive mechanism for moving the carrier stage and the sample slide relative to the light source such that successive portions of the sample slide are illuminated by the light source;
   a digital optical camera system arranged to operate in at least two modes, namely a diffraction or deflection mode, in which light rays diffracted or otherwise deflected at the array of samples on the sample slide are captured by a camera, and a fluorescent mode, in which light rays emitted from fluorescent markers on the array of samples are captured: wherein the digital optical camera system is arranged to operate in the deflection or diffraction mode when the drive mechanism moves the carrier stage in a first direction and is arranged to operate in the fluorescent mode when the drive mechanism moves the carrier stage in a second direction; wherein the digital optical camera system is disposed such that, in use, the digital optical camera system captures substantially only said successive portions of light rays which emerge from the sample slide at an offset angle relative to light rays from the light source transmitted through and emerging from the sample slide to generate a series of partial images arranged to be reconstructed into an image of the sample slide or array of samples.

2. An imaging device according to claim 1 wherein the light source is a linear light source arranged to emit a substantially narrow beam, whereby successive portions of the sample slide that are illuminated are band-like portions, and whereby the series of partial images are linear images.

3. An imaging device according to claim 1 wherein the digital optical camera system is disposed such that, in use, it receives substantially only light rays which are diffracted or otherwise deflected at said array of samples on the sample slide.

4. An imaging device according to claim 1 wherein the digital optical camera system includes a discriminator for preventing light rays which are not diffracted or otherwise deflected by the sample array from being captured by the camera system.

5. An imaging device according to claim 4 wherein the discriminator includes at least one reflector positioned to direct diffracted or otherwise deflected light rays emerging from the sample slide at the offset angle towards an imaging lens of the camera system.

6. An imaging device according to claim 4 wherein the digital optical camera system includes a line scan camera capable of sensing a linear image.

7. An imaging device as claimed in claim 1, wherein the digital optical camera system is disposed such that, in use, light rays emitted from fluorescent markers on the sample slide are captured.

8. An imaging device according to claim 1 wherein the optical camera system is arranged to detect light rays in both the visible and non-visible portions of the spectrum.

9. An imaging device as claimed in claim 1 wherein the samples comprise cells bound to binding partners on the sample slide.

10. An imaging device as claimed in claim 1, wherein the imaging device comprises a sampling compartment in which, in use, the carrier stage is located, and an electrical components compartment, wherein the electrical components compartment is fluid sealed from the sampling compartment, whereby, in use, fluid contamination of components inside the electrical components compartment from the sampling compartment is inhibited, the carrier stage including a tray element disposed, in use, underneath the sample slide for collecting fluid spilled from the sample slide.

11. An imaging device as claimed in claim 1, wherein the imaging device includes an interface unit for interfacing to at least one device selected from a group including an external reference database, an external storage database, an external PC, and an external printer.

12. An imaging device according to claim 6 wherein the line scan capable camera is a line scan camera adapted to scan linear images having a width of one pixel.

13. An imaging device according to claim 1 wherein the partial images and the reconstructed images are dark field images.

* * * * *